US010024841B2

(12) United States Patent
Meinert et al.

(10) Patent No.: US 10,024,841 B2
(45) Date of Patent: Jul. 17, 2018

(54) DEVICE FOR TESTING THE PROPERTIES OF FIBRES

(71) Applicant: The Procter & Gamble Company, Cincinnati, OH (US)

(72) Inventors: Knut Meinert, Lampertheim (DE); Gerhard Schanz, Darmstadt (DE); Marianne Jung, Morfelden-Walldorf (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/839,014

(22) Filed: Aug. 28, 2015

(65) Prior Publication Data
US 2016/0061809 A1    Mar. 3, 2016

(30) Foreign Application Priority Data

Aug. 29, 2014  (EP) .................................... 14182793

(51) Int. Cl.
*G01N 33/483* (2006.01)
*G01N 3/08* (2006.01)
*G01N 19/02* (2006.01)

(52) U.S. Cl.
CPC ........... *G01N 33/4833* (2013.01); *G01N 3/08* (2013.01); *G01N 19/02* (2013.01)

(58) Field of Classification Search
None
See application file for complete search history.

(56) References Cited

U.S. PATENT DOCUMENTS

| D12,422 | S | 8/1881 | Brundige |
| 311,445 | A | 1/1885 | Philippart |
| D26,313 | S | 11/1896 | Rosenthal |
| D35,952 | S | 6/1902 | Taylor |
| 1,335,163 | A | 3/1920 | Haag |
| D74,881 | S | 4/1928 | Haley |
| D96,714 | S | 8/1935 | Wewetzer |
| 2,085,238 | A | 6/1937 | Towell |
| D106,595 | S | 10/1937 | Hirsch |
| D110,176 | S | 6/1938 | Donchian |
| D114,501 | S | 4/1939 | Graff |

(Continued)

FOREIGN PATENT DOCUMENTS

| CN | 3143402 | 3/2000 |
| DE | 10259199 A1 | 6/2004 |

(Continued)

OTHER PUBLICATIONS

Vaynberg; The Aqualon SLT: A Novel Device for Measuring Hair Stiffness and Lubricity; J. Cosmet. Sci., 60, 135-141 (Mar./Apr. 2009); 7 pages.

(Continued)

*Primary Examiner* — Andre Allen
(74) *Attorney, Agent, or Firm* — Alexandra S. Anoff

(57) ABSTRACT

The present invention relates to a device for testing the properties of fiber(s). The fibers may be human hair fibers, for example, a hair tress. The device has a plurality of rods that are capable of freely rotating. Each rod has a proximal end and a distal end. The proximal end is connected to a support. The distal end is free. The present invention also relates to related uses and methods of using the device.

14 Claims, 11 Drawing Sheets

(56) References Cited

U.S. PATENT DOCUMENTS

| | | |
|---|---|---|
| D179,544 S | 1/1957 | Mayer |
| 2,978,077 A | 4/1961 | Wood |
| 3,143,259 A | 8/1964 | Paar |
| 3,472,243 A | 10/1969 | Wall |
| 3,472,604 A | 10/1969 | Dasher et al. |
| 3,492,191 A | 1/1970 | Horn et al. |
| 3,537,809 A | 11/1970 | Cednas |
| 3,577,518 A | 5/1971 | Shepherd et al. |
| 3,583,408 A | 6/1971 | Wall |
| D222,025 S | 9/1971 | Whitaker |
| 3,619,114 A | 11/1971 | Anzuino et al. |
| 3,619,117 A | 11/1971 | Anzuino et al. |
| 3,619,118 A | 11/1971 | Anzuino et al. |
| 3,633,591 A | 1/1972 | Anzuino et al. |
| 3,634,022 A | 1/1972 | Robbins et al. |
| 3,661,161 A | 5/1972 | Kalopissis et al. |
| 3,676,550 A | 7/1972 | Anzuino |
| 3,678,157 A | 7/1972 | Kalopissis et al. |
| 3,792,982 A | 2/1974 | David |
| 3,820,550 A | 6/1974 | Kinney et al. |
| 3,878,638 A | 4/1975 | Benjamin |
| 3,882,114 A | 5/1975 | Kalopissis et al. |
| 3,909,195 A | 9/1975 | Machell et al. |
| D238,537 S | 1/1976 | Longacre |
| 3,937,802 A | 2/1976 | Fujimoto et al. |
| 3,961,879 A | 6/1976 | Bugaut et al. |
| 4,152,416 A | 5/1979 | Spitzer et al. |
| D256,756 S | 9/1980 | Painter et al. |
| 4,278,659 A | 7/1981 | Breuer |
| 4,338,295 A | 7/1982 | Highley et al. |
| 4,448,832 A | 5/1984 | Kidwell |
| D276,143 S | 10/1984 | Williams |
| 4,548,324 A | 10/1985 | Mackey, Jr. |
| 4,588,760 A | 5/1986 | Jachowicz et al. |
| 4,610,261 A | 9/1986 | Madrange et al. |
| 4,719,104 A | 1/1988 | Patel |
| 4,726,945 A | 2/1988 | Patel et al. |
| D295,731 S | 5/1988 | Mancel |
| 4,792,470 A | 12/1988 | Clark |
| 4,961,439 A | 10/1990 | Hartmann |
| 5,002,761 A | 3/1991 | Mueller et al. |
| 5,008,140 A | 4/1991 | Schmertz |
| D332,160 S | 12/1992 | Kuzma |
| D338,809 S | 8/1993 | Bennett |
| D346,083 S | 4/1994 | Bareiss |
| 5,362,486 A | 11/1994 | Nandagiri et al. |
| 5,396,005 A | 3/1995 | Arhancet |
| 5,485,647 A | 1/1996 | Durst |
| D368,981 S | 4/1996 | Bozak |
| 5,538,720 A | 7/1996 | Jendryssek-Pfaff et al. |
| 5,596,038 A | 1/1997 | Subramaniam |
| D378,446 S | 3/1997 | Lutzker |
| 5,635,168 A | 6/1997 | Burns et al. |
| D383,568 S | 9/1997 | Giedd |
| D384,862 S | 10/1997 | Hayes et al. |
| D391,097 S | 2/1998 | Eichert et al. |
| D395,182 S | 6/1998 | Singleton |
| D399,160 S | 10/1998 | Pandel |
| 5,819,960 A | 10/1998 | Bonazza |
| 5,855,208 A | 1/1999 | Askill et al. |
| D408,223 S | 4/1999 | Henry |
| 6,027,819 A | 2/2000 | Mosely |
| 6,073,634 A | 6/2000 | Gueret |
| 6,076,531 A | 6/2000 | Gueret |
| D432,868 S | 10/2000 | Tan |
| 6,141,034 A | 10/2000 | McCutchen |
| D433,879 S | 11/2000 | Emrani |
| 6,143,805 A | 11/2000 | Hickey et al. |
| 6,172,665 B1 | 1/2001 | Bullister |
| D441,536 S | 5/2001 | Jackson-MacDonald |
| D449,712 S | 10/2001 | Glemain |
| D449,792 S | 10/2001 | Nadeau et al. |
| D461,102 S | 8/2002 | Suzuki |
| D463,317 S | 9/2002 | Bull |
| 6,482,808 B1 | 11/2002 | Springob et al. |
| 6,586,493 B1 | 7/2003 | Massia et al. |
| D480,325 S | 10/2003 | Bull |
| D483,688 S | 12/2003 | Kent et al. |
| D487,034 S | 2/2004 | Lach |
| 6,709,648 B2 | 3/2004 | Sako et al. |
| 6,740,317 B1 | 5/2004 | Cho et al. |
| 6,783,815 B2 | 8/2004 | Flohe |
| D502,786 S | 3/2005 | Cheung |
| D505,639 S | 5/2005 | Lach |
| D505,640 S | 5/2005 | Star |
| 6,921,574 B2 | 7/2005 | Cinelli et al. |
| D511,912 S | 11/2005 | Blonder |
| D513,934 S | 1/2006 | Warner |
| D521,740 S | 5/2006 | Pryor |
| D532,258 S | 11/2006 | Bardolet |
| 7,159,728 B2 | 1/2007 | Smith |
| D538,997 S | 3/2007 | Schlembach |
| 7,255,869 B2 | 8/2007 | Uchida et al. |
| 7,261,948 B2 | 8/2007 | Edkins |
| D552,423 S | 10/2007 | Friedland et al. |
| D563,263 S | 3/2008 | Chen |
| D577,615 S | 9/2008 | Markfelder |
| D578,829 S | 10/2008 | Freeman |
| 7,472,577 B2 | 1/2009 | Shibuichi |
| D592,495 S | 5/2009 | Reiterer et al. |
| D605,353 S | 12/2009 | Lee et al. |
| D625,956 S | 10/2010 | Goddard-Clark et al. |
| D630,799 S | 1/2011 | Greiner |
| 7,981,167 B2 | 7/2011 | Carballada et al. |
| D642,741 S | 8/2011 | Greiner |
| D644,039 S | 8/2011 | Naples et al. |
| D647,726 S | 11/2011 | Strauch |
| 8,048,846 B2 | 11/2011 | Chahal et al. |
| D658,009 S | 4/2012 | Davis et al. |
| 8,168,576 B2 | 5/2012 | Hoffmann et al. |
| D681,344 S | 5/2013 | Davis et al. |
| D687,183 S | 7/2013 | Davis et al. |
| 9,358,197 B2 | 6/2016 | Flohr et al. |
| 2001/0015399 A1 | 8/2001 | LaMotte |
| 2001/0029636 A1 | 10/2001 | Brownbill et al. |
| 2001/0032019 A1 | 10/2001 | Van Dyke et al. |
| 2002/0015718 A1 | 2/2002 | Kruse et al. |
| 2002/0026005 A1 | 2/2002 | Munro |
| 2002/0055962 A1 | 5/2002 | Schroeppel |
| 2003/0103930 A1 | 6/2003 | Uchida et al. |
| 2003/0175229 A1 | 9/2003 | Giroud |
| 2003/0212416 A1 | 11/2003 | Cinelli et al. |
| 2003/0235554 A1 | 12/2003 | Chahal |
| 2004/0016062 A1 | 1/2004 | Plos |
| 2004/0018162 A1 | 1/2004 | Bimczok et al. |
| 2004/0028626 A1 | 2/2004 | Candau |
| 2004/0156800 A1 | 8/2004 | Brun et al. |
| 2004/0166071 A1 | 8/2004 | Pfaffernoschke et al. |
| 2004/0191316 A1 | 9/2004 | Sasahara et al. |
| 2004/0235700 A1 | 11/2004 | Legrand et al. |
| 2004/0261198 A1 | 12/2004 | Kainz et al. |
| 2005/0042196 A1 | 2/2005 | Askill et al. |
| 2005/0078523 A1 | 4/2005 | Lee et al. |
| 2005/0129652 A1 | 6/2005 | Keller et al. |
| 2005/0188998 A1 | 9/2005 | Salas |
| 2006/0078522 A1 | 4/2006 | Vic |
| 2006/0233996 A1 | 10/2006 | Oakey et al. |
| 2006/0235947 A1 | 10/2006 | Gray et al. |
| 2006/0237696 A1 | 10/2006 | Gourlaouen et al. |
| 2007/0066506 A1 | 3/2007 | Behler et al. |
| 2007/0202065 A1 | 8/2007 | Devin-Baudoin et al. |
| 2007/0253927 A1 | 11/2007 | Jegou et al. |
| 2007/0259794 A1 | 11/2007 | Wachsberg |
| 2007/0261179 A1 | 11/2007 | Dorkel et al. |
| 2007/0275020 A1 | 11/2007 | Lendlein et al. |
| 2007/0277332 A1 | 12/2007 | Bimczok et al. |
| 2008/0025936 A1 | 1/2008 | Keller et al. |
| 2008/0066773 A1 | 3/2008 | Anderson et al. |
| 2008/0187506 A1 | 8/2008 | Carballada et al. |
| 2008/0210253 A1 | 9/2008 | Carballada et al. |
| 2008/0311050 A1 | 12/2008 | Lendlein et al. |
| 2009/0022681 A1 | 1/2009 | Carballada et al. |
| 2009/0283106 A1 | 11/2009 | Torgerson et al. |
| 2010/0028279 A1 | 2/2010 | Carballada et al. |

(56) References Cited

U.S. PATENT DOCUMENTS

| | | |
|---|---|---|
| 2010/0028286 A1 | 2/2010 | Carballada et al. |
| 2010/0095974 A1 | 4/2010 | Laje |
| 2011/0008265 A1 | 1/2011 | Anderson et al. |
| 2011/0064684 A1 | 3/2011 | Krause et al. |
| 2011/0070179 A1 | 3/2011 | Puerta et al. |
| 2011/0126850 A1 | 6/2011 | Hoffmann et al. |
| 2011/0229429 A1 | 9/2011 | Hoffmann et al. |
| 2012/0180807 A1 | 7/2012 | Flohr |
| 2012/0183486 A1 | 7/2012 | Flohr et al. |
| 2012/0192893 A1 | 8/2012 | Anderson |
| 2013/0058882 A1 | 3/2013 | Flohr et al. |
| 2014/0041678 A1 | 2/2014 | Flohr et al. |
| 2014/0209843 A1* | 7/2014 | Devine ............. H02G 1/02 254/134.3 R |
| 2014/0356305 A1 | 12/2014 | Carballada et al. |
| 2015/0320658 A1 | 11/2015 | Flohr et al. |
| 2016/0061809 A1 | 3/2016 | Meinert et al. |
| 2016/0317411 A1 | 11/2016 | Flohr et al. |
| 2017/0165173 A1 | 6/2017 | Flohr et al. |
| 2017/0165174 A1 | 6/2017 | Flohr et al. |

FOREIGN PATENT DOCUMENTS

| | | |
|---|---|---|
| EP | 0173195 B1 | 5/1990 |
| EP | 0716846 A1 | 6/1996 |
| EP | 000044748-0001 | 10/2003 |
| EP | 000044748-0002 | 10/2003 |
| EP | 000334081-0001 | 7/2005 |
| EP | 000334081-0002 | 7/2005 |
| EP | 001505553-0001 | 6/2009 |
| EP | 001505553-0002 | 6/2009 |
| EP | 001505553-0003 | 6/2009 |
| EP | 2772246 A1 | 9/2014 |
| ES | D0500996-02 | 6/2005 |
| FR | 2902320 A1 | 12/2007 |
| GB | 2060843 | 3/1997 |
| GB | 2073898 | 8/1998 |
| GB | 2086666 | 12/1999 |
| GB | 3022892 | 11/2005 |
| JP | 5338634 A | 4/1978 |
| JP | 62209006 A | 9/1987 |
| JP | 03020205 A | 1/1991 |
| JP | H04208214 | 7/1992 |
| JP | 10279436 A | 10/1998 |
| JP | 2000302648 A | 10/2000 |
| WO | WOD038500-001 | 2/1997 |
| WO | WO0045777 A1 | 8/2000 |
| WO | WO0213773 A2 | 2/2002 |
| WO | WO0245665 A1 | 6/2002 |
| WO | WO2004062633 A1 | 7/2004 |
| WO | WOD037902-001 | 6/2005 |
| WO | WO2013188198 A3 | 10/2014 |

OTHER PUBLICATIONS

Fujii; Bearings with Solid Lubricants; Koyo Engineering Journal (English Edition); vol. 164E, Mar. 31 2004, pp. 24-29.
"Organic isomers", http://faculty.lacitycollege.edu/boanta/LAB102/Organic%20Isomers.htm, accessed May 12, 2015.
3-sulfopropyl acrylate potassium salt. hftp://sigmaaldrich.com/catalog/productDetail.do?D7=0&N5=Product%20No.%7CBrand_KEY&N4=25163%7CALDRICH&N25=0&QS=ON&F=SPEC. Accessed Nov. 18, 2009.
All Final and Non-Final Office Actions, U.S. Appl. No. 11/702,308.
All Final and Non-Final Office Actions, U.S. Appl. No. 11/978,899.
All Final and Non-Final Office Actions, U.S. Appl. No. 12/183,686.
All Final and Non-Final Office Actions, U.S. Appl. No. 12/507,214.
All Final and Non-Final Office Actions, U.S. Appl. No. 12/507,221.
All Final and Non-Final Office Actions, U.S. Appl. No. 12/881,763.
All Final and Non-Final Office Actions, U.S. Appl. No. 13/353,843.
Final and Non-Final Office Actions, U.S. Appl. No. 13/353,985.
Final and Non-Final Office Actions, U.S. Appl. No. 13/918,061.
Final and Non-Final Office Actions, U.S. Appl. No. 13/598,866.
Final and Non-Final Office Actions, U.S. Appl. No. 14/462,022.
Final and Non-Final Office Actions, U.S. Appl. No. 15/142,164.
Final and Non-Final Office Actions, U.S. Appl. No. 29/397,767.
Final and Non-Final Office Actions, U.S. Appl. No. 29/397,768.
Final and Non-Final Office Actions, U.S. Appl. No. 29/397,769.
Final and Non-Final Office Actions, U.S. Appl. No. 29/397,771.
Final and Non-Final Office Actions, U.S. Appl. No. 29/397,774.
All Office Actions, U.S. Appl. No. 14/707,584.
Amino Acids, https://web.archive.org/web/20030326022411/http://www.imagerynet.com/amino/20_amino.html. Published Mar. 26, 2003.
Anonymous: Carbowax™ Polyethylene Glycols Innovation, Performance, Flexibility and Quality from the Global Leader in PEGs; Oct. 2011.
Database GNPD; Mintel: Herbal Hair Moisturiser, Aug. 2001.
Definition "Under", Merriam-Webster Dictionary Online, http://www.merriam-webster.com/dictionary/under, retrieved online Apr. 17, 2003.
Dia Curit & Wavy Hair Shampoo Product Description.
Ethylene glycol di methacrylate. http://www.ecem.com/sales/data/EGDMA.HTM. Accessed Nov. 18, 2009.
http://chem.answers.com/compounds/basic-facts-about-butylated-hydroxyanisole-or-bha as referenced on May 15, 2014.
http://www.sigmaaldrich.com/catalog/product/aldrich/20021?lang=en&region=US referenced on Nov. 9, 2015.
Ionic Radii Table, Physical Chemistry Sixth Edition, P.W. Atkins, 3 pages.
LookChem reference [Retrieved on Dec. 17, 2010 from the Internet: <URL: http://www.lookchem.com/cas-310/31098-20-1.html].
Methylene-bis-acrylamide. http://east.cherryhill.k12.nj.us/msds/M/Methylene-bis-Acrylamide.pdf, accessed Nov. 18, 2009.
Mr. Grand Styling Wax Product Description.
Paul Labrecque Daily Finish Matte Pomade Product Description.
PCT International Search Report and Written Opinion for PCT/US2012/032046 dated May 9, 2012.
PCT International Search Report and Written Opinion for PCT/US2012/052966 dated Jul. 5, 2013.
PCT International Search Report and Written Opinion for PCT/US2013/044405 dated Aug. 7, 2014.
PCT International Search Report and Written Opinion for PCT/US2015/029821 dated Aug. 13, 2015.
Sartomer. http://www.sartomer.com/TechLit/5015.pdf. Accessed on Nov. 18, 2009.

* cited by examiner

DEVICE FOR TESTING THE PROPERTIES OF FIBRES

FIELD OF THE INVENTION

Device for testing the properties of fibre(s), particularly human hair fibres such as a hair tress. Also associated methods and uses. Such a device can be used for research and development into improved cosmetic hair products.

BACKGROUND OF THE INVENTION

Cosmetic hair products aim to alter the appearance, feel and/or manageability of hair. For example, hair conditioners typically reduce hair fibre-fibre friction by use of cationic ingredients which are substantive to hair due to the isoelectric point of hair being around pH 3.67 (Robbins, C. R., Chemical and Physical Behavior of Human Hair, $4^{th}$ Ed., Springer, 2002, p. 351). Hair styling agents also alter the manageability of hair, for example in Flohr et al. US2012/0183486A1 discloses a "composition for chemically modifying the internal region of a hair shaft" and states in § 54 that "an increase in weight occurs following treatment of hair by a composition of the present invention and that the physical properties of the hair, namely its stiffness, are increased, and moreover, these changes being resistant to wash out". Hair colourants, perming agents and methods for straightening hair also typically alter the mechanical properties and surface of hair fibres in addition to their main functions—dyeing, curling and straightening the fibres, respectively. In the modern age, consumers demand high performance from the cosmetic hair products that they buy and the service they pay for in salon. Indeed, the desire for improved performance and combination effects e.g. dyeing and conditioning is continually increasing.

As a result of these changes in mechanical and surface properties of the hair fibres, methods and devices are used to measure these properties of hair. The measurements are useful for providing feedback to consumers as to the properties and healthiness of their hair fibres and also to guide research and development of new cosmetic hair products to provide improved performance. Krause et al. EP2295029A1, for example, discloses an "'Omega Loop' Measurement" in § 73 and 74 and states that the "amount of force necessary to compress the hair a defined distance is measured". Other methods are mentioned in Robbins from pages 413 to 418 (Robbins, C. R., Chemical and Physical Behavior of Human Hair, $4^{th}$ Ed., Springer, 2002, p. 351). Reference Vaynberg and Nall, *J. Cosmet. Sci.*, 60, 135-141 (March/April 2009)—hereinafter referred to as "Vaynberg and Nall"—discloses a device that allows hair scientists to measure hair tress changes in stiffness and lubricity.

Nevertheless there is an unmet need for improved devices and methods for measuring the properties of fibres, particularly human hair fibres. Particularly, there is a desire for devices and methods that are more sensitive and can distinguish between small and incremental improvements in mechanical and surface properties of fibres. Indeed, the human hand is highly sensitive and can detect tiny changes in hair fibre friction and stiffness—thus small and incremental improvements in the performance of hair cosmetic products can result in a highly improved consumer experience.

SUMMARY OF THE INVENTION

In a first aspect, the present invention relates to a device 1 for testing the properties of fibre(s) 2 comprising:
a plurality of rods 3 that are capable of freely rotating;
wherein each rod 3 has a proximal end 4 and a distal end 5;
wherein the proximal end 4 is connected to a support 6; characterised in that the distal end 5 is free.

In a second aspect, the invention relates to the use of a device 1 according to the first aspect for testing the properties of fibres 2.

In a second aspect, the invention relates to a method for testing the properties of fibre(s) 2 comprising:
(a) providing a device according to the first aspect, and providing fibres 2;
(b) threading the fibres 2 through the plurality of rods 3 between the fibre-guiding means 7;
(c) by use of a fibre-pulling means 10, passing the fibres 2 through the device 1 and simultaneously measuring the force required to do this.

BRIEF DESCRIPTION OF THE DRAWINGS

Key to Reference Signs 1. device
2. fibres
3. rod
4. proximal end (of rod)
5. distal end (of rod)
6. support
7. fibre-guiding means
8. housing
9. ball bearings
10. fibre-pulling means
11. blocking mechanism
12. blocking lever
13. void
14. plate
15. cap
16. pin
17. roughened portion
18. housing orifice
19. inner bearing seat
20. outer bearing seat Figures

DETAILED DESCRIPTION OF THE INVENTION

Figure 1:
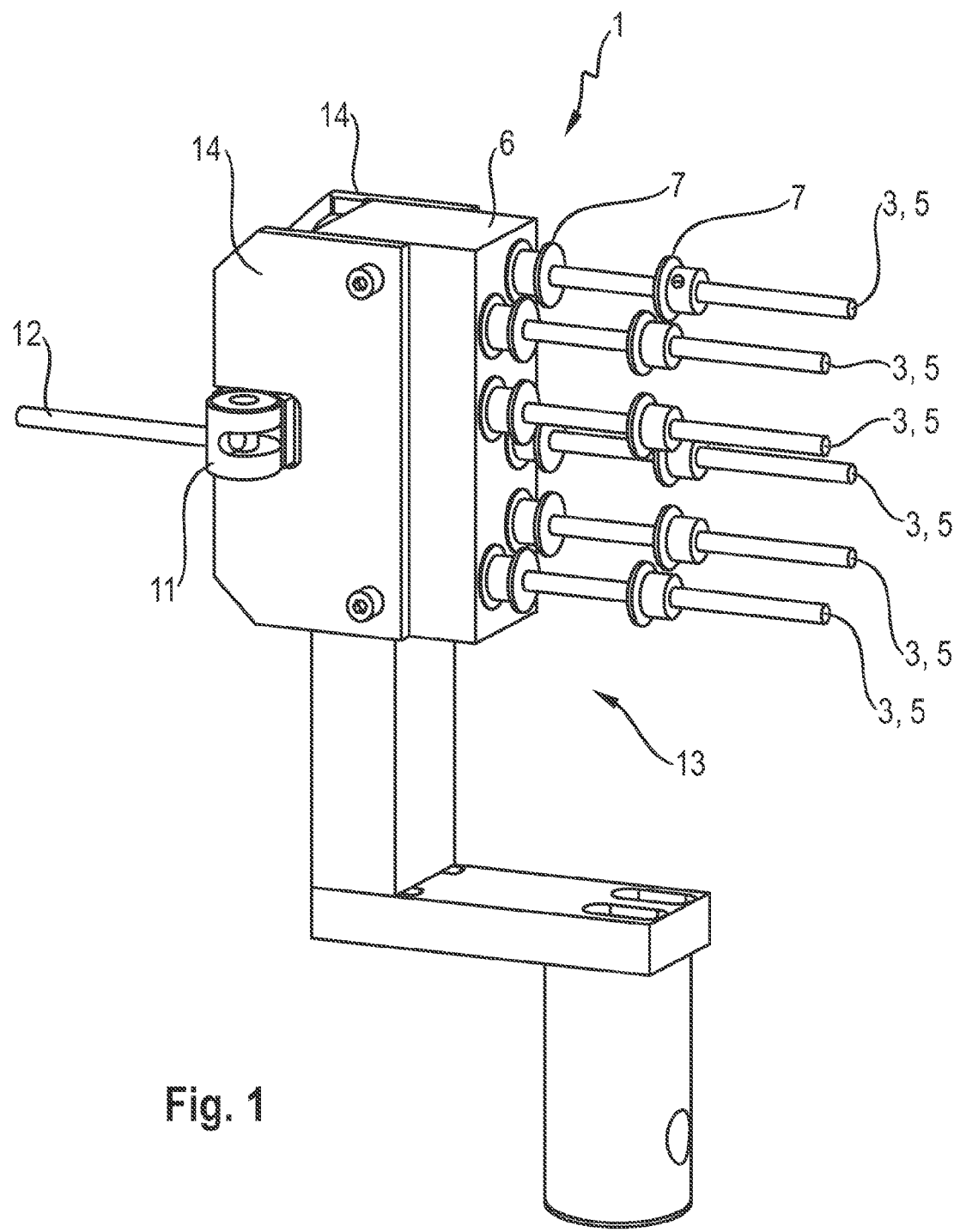
FIG. 1: Schematic representation of a device 1 according to the present invention. The device comprises six rods 3. The fibre(s) 2 are not depicted.
Figure 2:
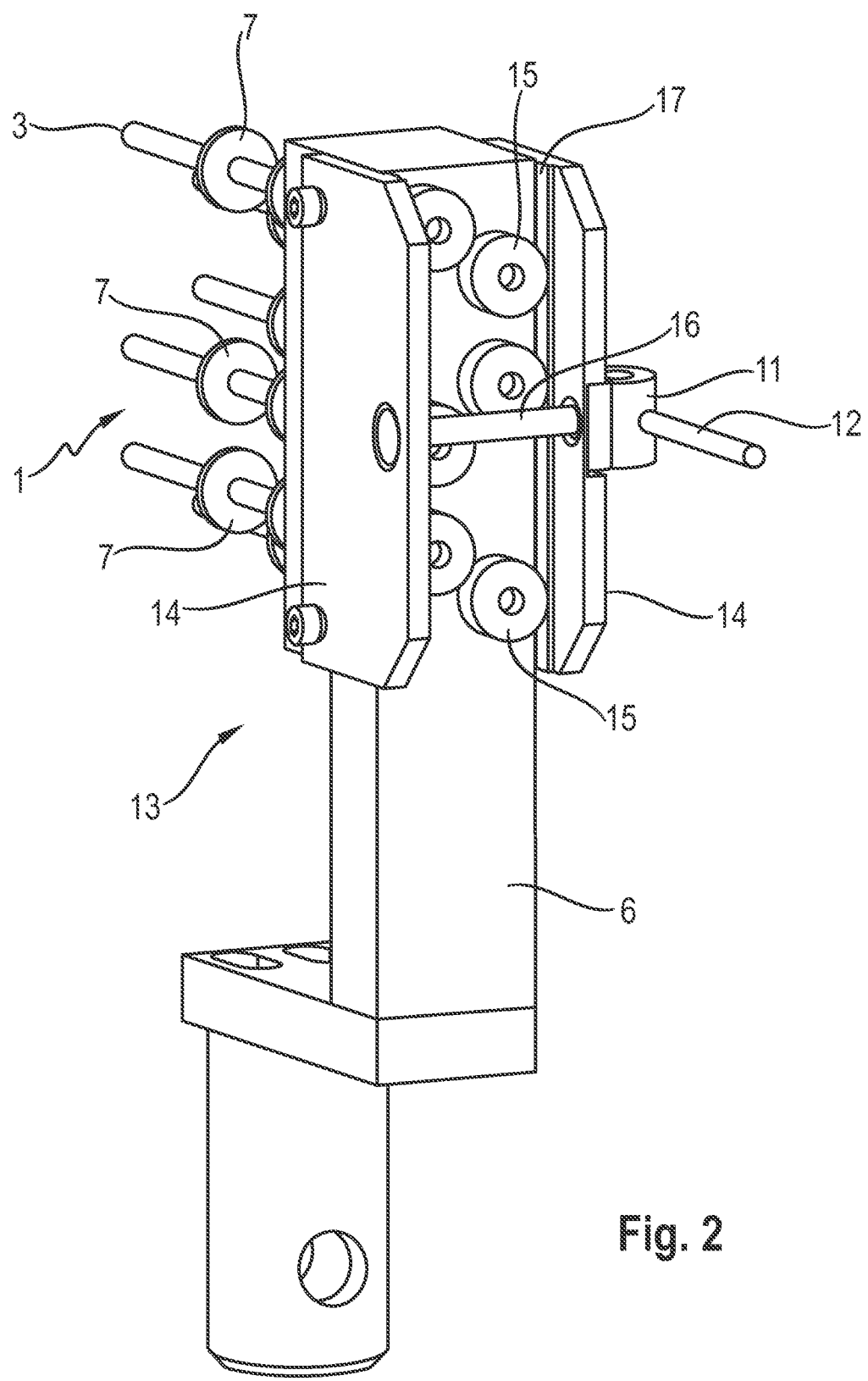
FIG. 2: Device 1 as in FIG. 1, but angled side view.
Figure 3:
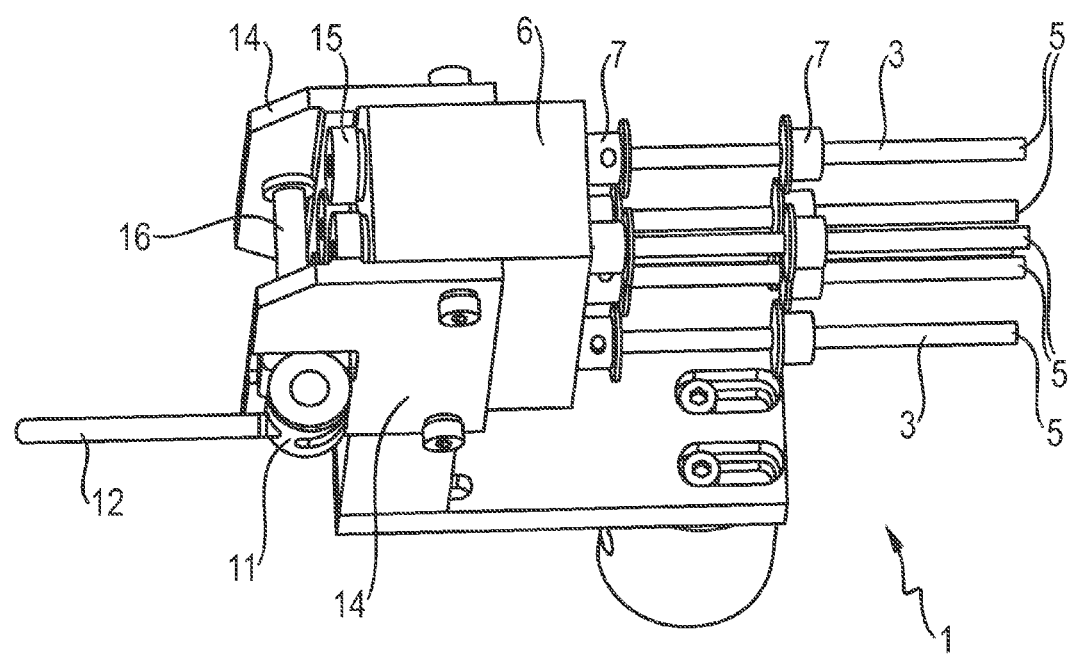
FIG. 3: Device 1 as in FIG. 1, but view from above.

In this document, including in all embodiments of all aspects of the present invention, the following definitions apply unless specifically stated otherwise. All percentages are by weight of the total composition. All ratios are weight ratios. References to 'parts' e.g. a mixture of 1 part X and 3 parts Y, is a ratio by weight. "QS" or "QSP" means sufficient quantity for 100%. +/− indicates the standard deviation. All ranges are inclusive and combinable. The number of significant digits conveys neither a limitation on the indicated amounts nor on the accuracy of the measurements. All numerical amounts are understood to be modified by the word "about". All measurements are understood to be made at 25° C. and at ambient conditions, where "ambient conditions" means at 1 atmosphere (atm) of pressure and at 65% relative humidity. "Relative humidity" (RH) refers to the ratio (stated as a percent) of the moisture content of air compared to the saturated moisture level at the same temperature and pressure. Relative humidity can be measured with a hygrometer, for example with a probe hygrometer from VWR® International. Herein "min" means "minute" or "minutes". Herein "mol" means mole. Herein "g" following a number means "gram" or "grams". All weights as they pertain to listed ingredients are based on the active level and do not include carriers or by-products that may be included in commercially available materials. Herein, "comprising" means that other steps and other ingredients can be in addition. "Comprising" encompasses the terms "consisting of" and "consisting essentially of". Any compositions, formulations, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated. "In at least one embodiment" means that one or more embodiments of the invention, for example all embodiments or optionally a large subset of embodiments, has/have the subsequently described feature.

"Hair" means mammalian keratin fibres including scalp hair, facial hair and body hair. It includes such hair still being attached to a living subject and also hair that has been removed therefrom such as hair swatches and hair on a doll/mannequin. In an embodiment, "hair" means human hair. "Hair shaft" or "hair fibre" means an individual hair strand and may be used interchangeably with the term "hair."

The present invention relates inter alia to a device 1 for testing the properties of fibre(s) 2.

Rods

The device 1 comprises a plurality of rods 3. The plurality of rods 3 are for bending the fibre(s) 2. The rods 3 are capable of freely rotating; wherein each rod 3 has a proximal end 4 and a distal end 5; wherein the distal end 5 is free. In at least one embodiment, the plurality of rods 3 are arranged such that the distal ends 5 are arranged on the same side of the device 1.

The distal end 5 being free provides a significant advantage over the prior art: in particular there is better accessibility to the device 1 for the user when passing the fibres 2 between the rods 3—this is due to open design at one side of the device 1. This better accessibility enables a wider variety of arrangements for the plurality of rods 3 in terms of their proximity to one another and also placement versus one another—see, for example, FIG. 5. Indeed, in the instrument disclosed in Vaynberg and Nall, there is a solid housing on both sides of the rods that is used for hair tress guidance. This closed design means that the fibre(s) 2 would have to be thread through the "system of pins". In contrast, for the present invention, the fibre(s) 2 can be slid into the device laterally. For example, a tress of fibres 2 is usually buddled together by a gathering means at one end of the fibres e.g. by glueing all the fibres together or glueing them to a piece of resistant material. Consequently, the flexibility, size and thickness of this gathering means limits how the "system of pins" disclosed in Vaynberg and Nall can be arranged—the space between the pins must be able to accommodate this gathering means in order to thread the tress of fibres through the instrument of Vaynberg and Nall. The distal end 5 being free in the present invention overcomes this disadvantage.

In at least one embodiment, the distal end 5 consists of up to 50% of the length of the rod 3. In at least one embodiment, the proximal end 4 consists of up to 50% of the length of the rod 3.

It is useful that the rods 3 are capable of freely rotating. Herein "freely rotating" means rotation is hindered as little as possible.

The proximal end 4 is connected to a support 6.

Figure 9:
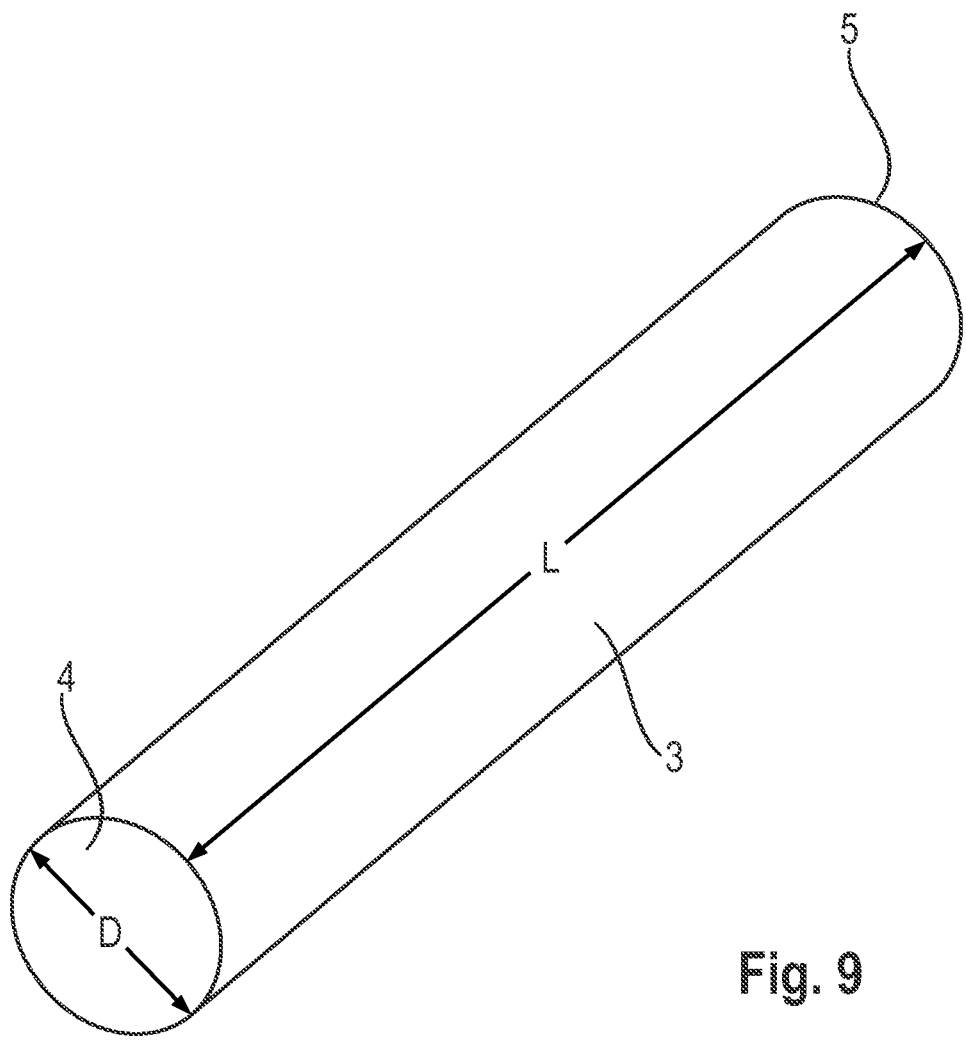
FIG. 9: A rod 3 is depicted. Length L is shown and also diameter D.

In at least one embodiment, a rod 3 is cylindrical, or all rods 3 are cylindrical. A cylindrical rod 3 is depicted in FIG. 9. In at least one embodiment, each rod 3 of the plurality of rods 3 has an average length L. Average length L is parallel to the axis of the rod 3. The average length L may be calculated by measuring the length L as depicted in FIG. 9 at five different points on the surface of the rod 3 and dividing by five to give the average length. Average length L is parallel to the axis of the rod 3. In at least one embodiment, L is from 7 cm to 25 cm, or from 8 cm to 22 cm, or from 10 cm to 20 cm, or from 11 cm to 18 cm, or from 12 cm to 16 cm. In at least one embodiment, L is from 10 cm to 20 cm. The average length L is important in view of ability to accommodate a tress of fibres 2, which are typically 2.5 cm wide or 5 cm wide, and also a significant portion, for example, at least 25% of length L, of the rod 3 being accommodated in the support 6 such that the rod 3 remains stable.

In at least one embodiment, each rod 3 has an average diameter D. The average length D may be calculated by measuring the diameter D as depicted in FIG. 9 at each end of the rod 3 and dividing by two to give the average diameter D. Average diameter D is perpendicular to the axis of the rod 3. In at least one embodiment, average diameter D is from 2 mm to 12 mm, or to 11 mm, or to 10 mm, or to 8 mm, or from 3 mm to 6 mm. In at least one embodiment, average diameter D is from 2 mm to 10 mm Vis-à-vis the average diameter D it is advantage if this value is not too low. Indeed, a rod 3 being too thin may not provide enough surface contact area for the fibre(s) 2 on each rod 3. However, a rod 3 being too thick (average diameter D value being too large), then the moment (torque) required for the fibre(s) 2 to move the rod 3 may be too high.

In at least one embodiment, the device 1 comprises at least two rods 3. In at least one embodiment, the device 1 comprises at least three, or at least four, or at least five, or at least six rods 3. In at least one embodiment, the device 1 comprises from two to eight rods 3, or from four to six rods 3. In at least one embodiment, the device 1 comprises from two to eight rods 3.

In at least one embodiment, the plurality of rods 3 are lengthwise substantially parallel to each other, or lengthwise parallel to each other. "Lengthwise parallel" means the lengths of each are parallel to one another.

Figure 5:
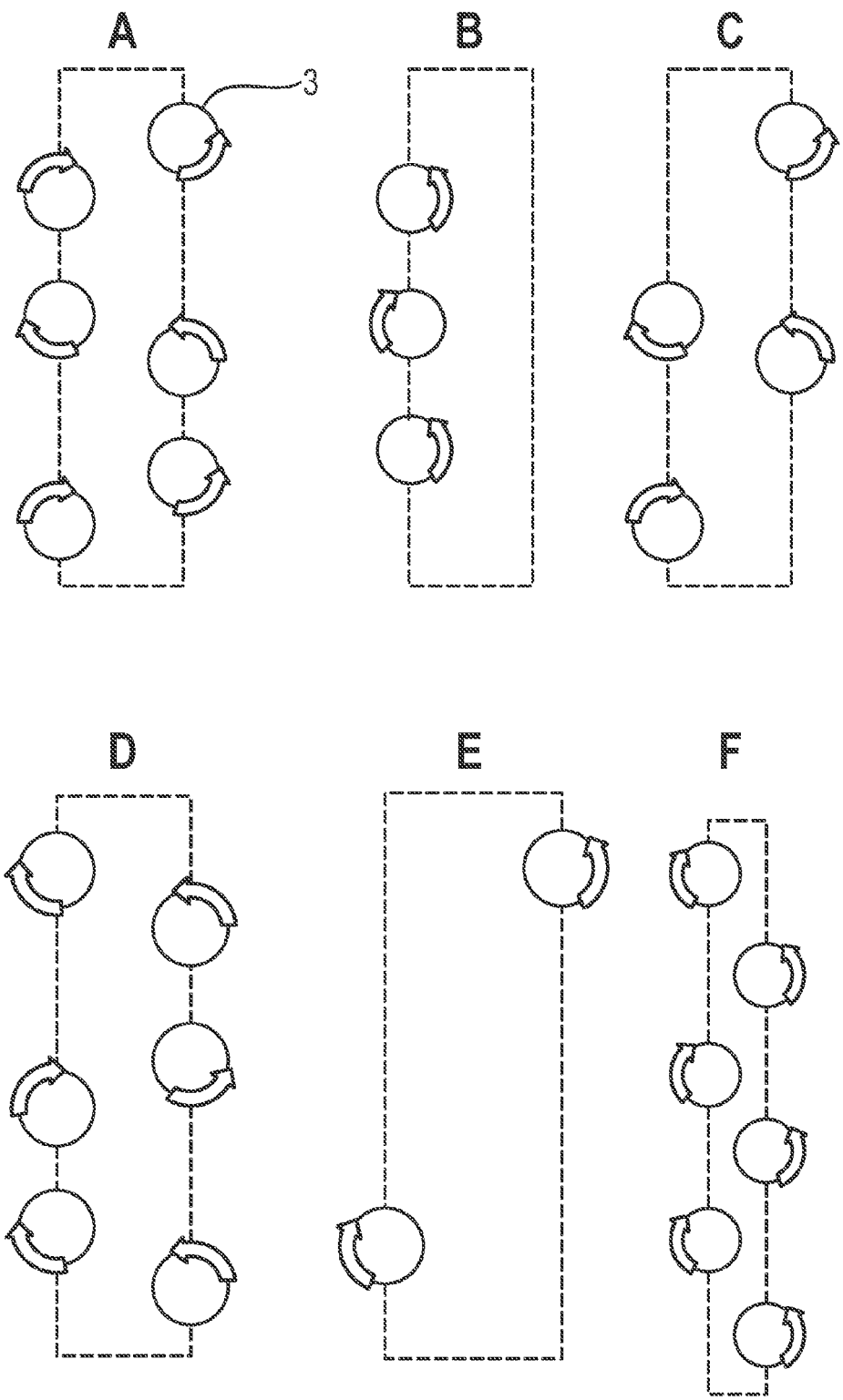
FIG. 5: Optional arrangement of rods 3. The path of fibre(s) 2 over the rod 3 is depicted via an arrow.
Figure 6:
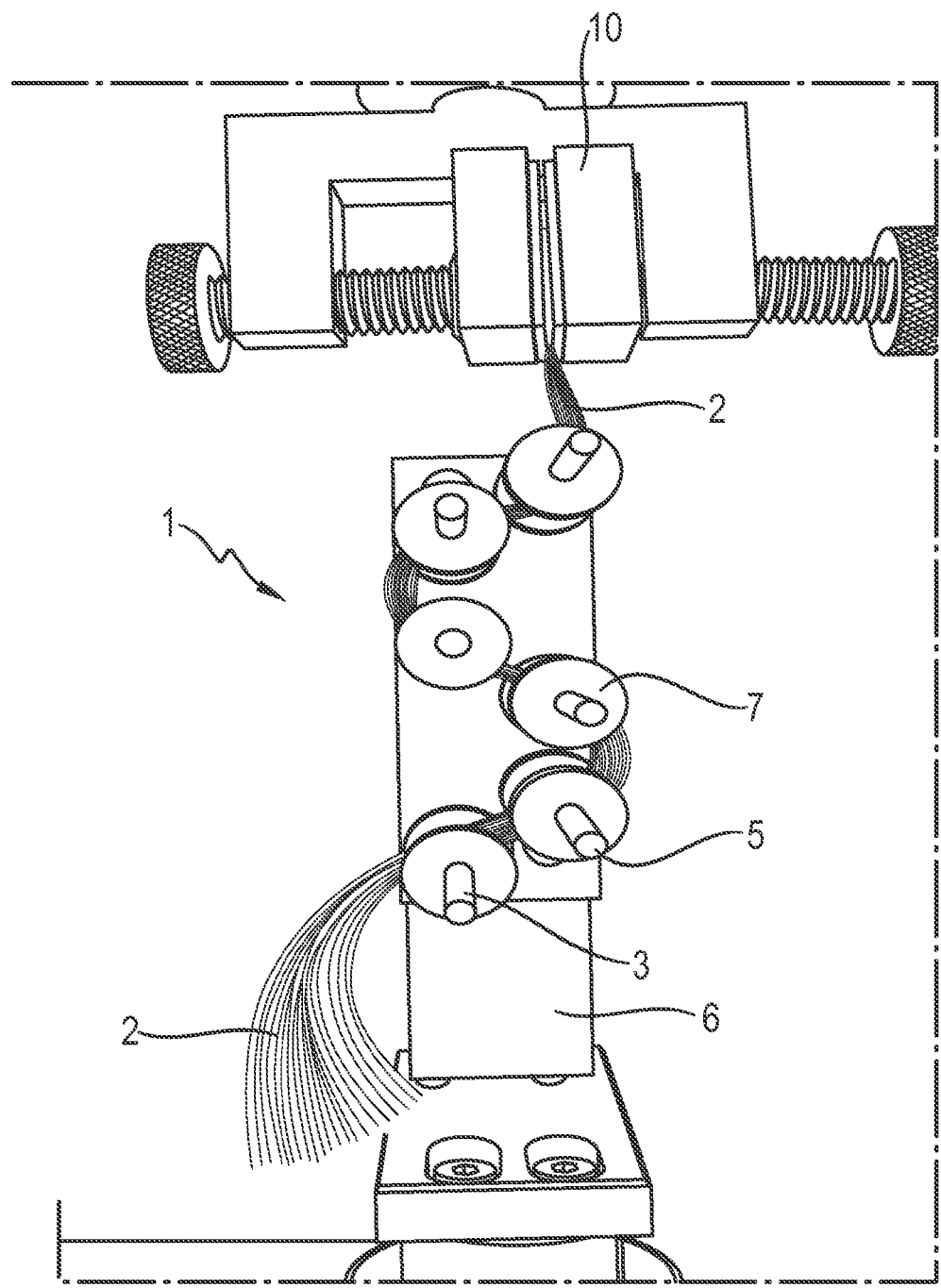
FIG. 6: Device 1 according to the present invention. A fibre-pulling means 10 is depicted. A tress of fibres 2 is also shown.
Figure 7:
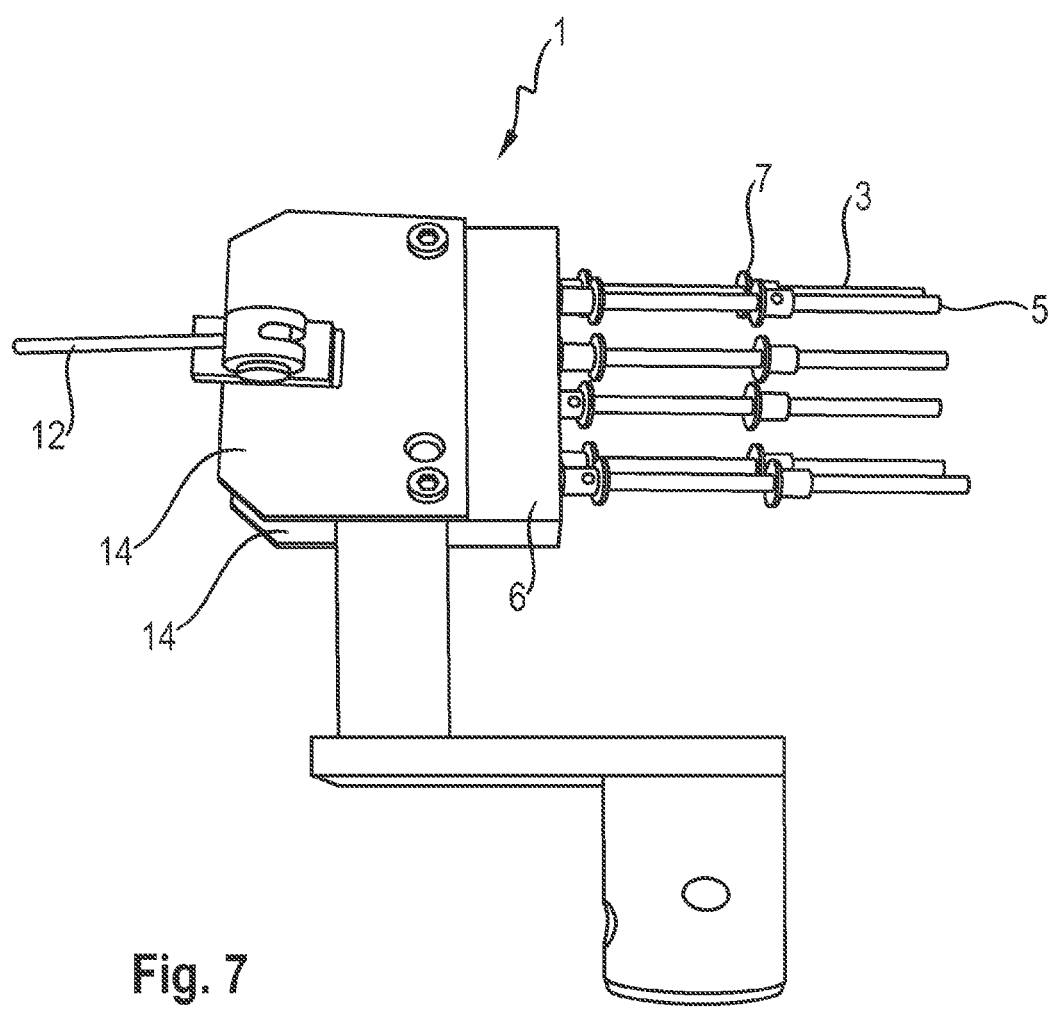
FIG. 7: Device 1 according to the present invention.
Figure 8:
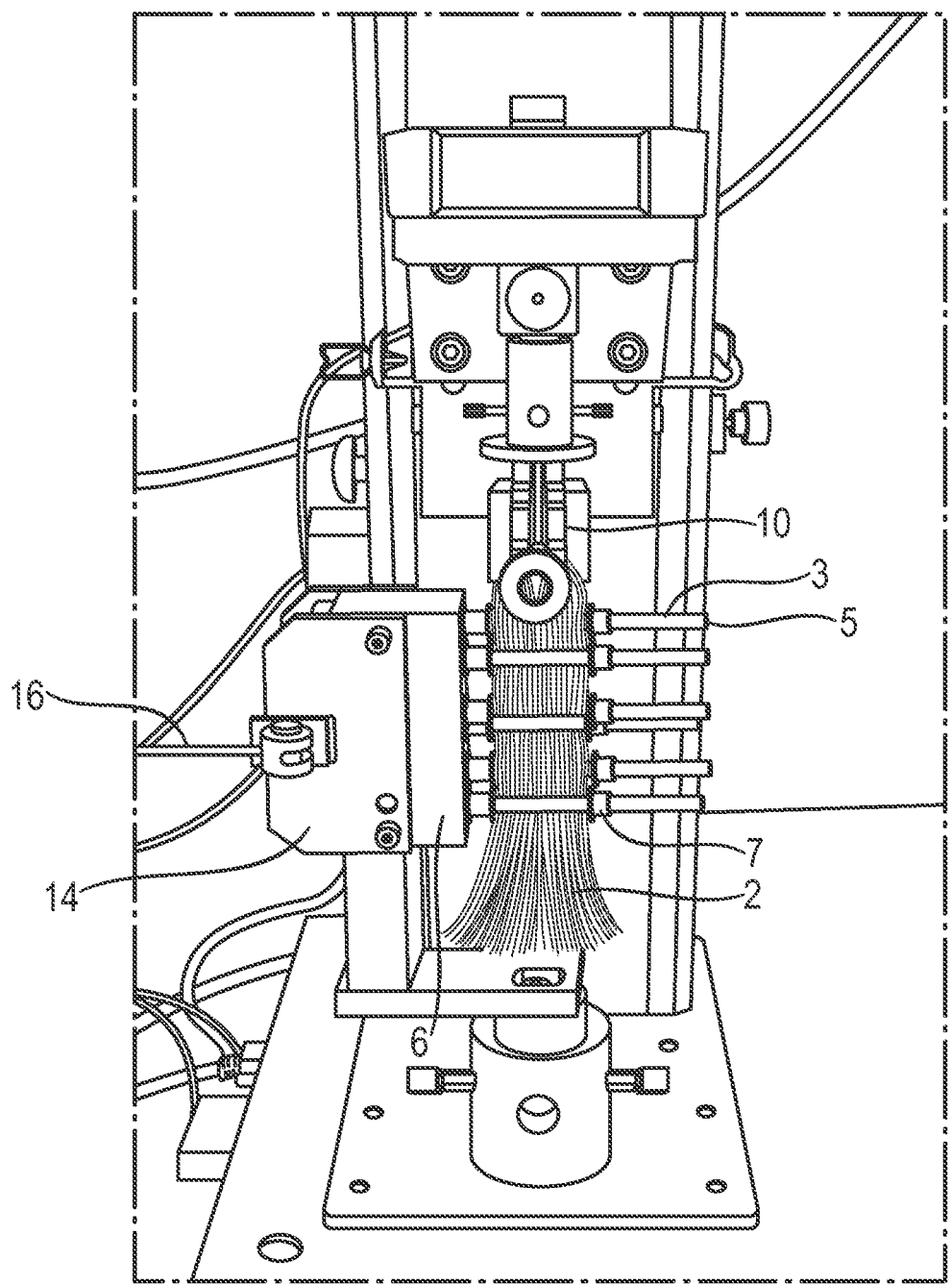
FIG. 8: Device 1 according to the present invention. A fibre-pulling means 10 is depicted. A tress of fibres 2 is also shown.

Exemplary arrangements of rods 3 when viewed from the distal end 5 side of the rods 3 are depicted in FIG. 5. In at least one embodiment, the plurality of rods 3, in concert, form two rows when viewed from the distal end 5 side of the rods 3. One row comprises at least two rods 3. Plurality of rods 3 arranged in two rows are depicted in FIGS. 5A, C, D and F. Since FIG. 5E contains only two rods 3, two rows are not illustrated. In at least one embodiment, the plurality of rods 3, in concert, form an S-shape when viewed from the distal end 5 side of the rods 3, or the mirror image of an S shape. An S-shape is depicted in FIG. 5A and a mirror image of an S-shape is shown in FIG. 5D. The arrangement of FIG. 5F comprises a mirror image of an S-shape as well as an S-shape.

In at least one embodiment, at least one rod 3, or all rods 3, are coated with a surface coating. In at least one embodiment, the surface coating comprises keratin, or is composed of keratin. In at least one embodiment, the surface coating is a skin mimic. In at least one embodiment, the skin mimic is be composed of silicone such as a silicone film, for example with surface texture (used for prosthetic limbs/skin), polyurethane, rubbery material, foam pads. In at least one embodiment, the surface coating is composed of silicone, polyurethane and/or rubber. In at least one embodiment, at least one rod 3, or all rods 3, have a removable sleeve over the rod 2. The removable sleeve can provide a surface coating.

In at least one embodiment, at least one rod 3, or the plurality of rods 3, are composed of a resistant material. In at least one embodiment, the resistant material is selected from the group consisting of: metal, ceramic, glass fibre enhanced resins, and carbon fibre reinforced resins. It is advantageous if the resistant material is reasonably stiff so it does not vibrate. In at least one embodiment, the plurality of rods 3 are composed of steel or aluminium. In at least one embodiment, the plurality of rods 3 are composed of stainless steel. In at least one embodiment, a rod 3, or plurality of rods 3, is/are hollow.

In at least one embodiment, at least one rod 3 is composed of a plurality of rod-shaped parts that are releasably attached to one another. The rod-shaped parts have the advantage that a rod 3 can be assembled from a plurality of rod-shaped parts. This provides a device 1 that is more accessible and convenient in that the one or more rods 3 can be assembled at a time that is most convenient. In at least one embodiment, at least one rod 3 is composed of a plurality of rod-shaped parts that are releasably attached via a screw and thread attachment.

In at least one embodiment, the surface of the rod 3 has an average roughness Rz, being from 0.5 μm to 5 μm, or from 1.0 μm to 4.0 μm, or from 2.0 μm to 3.0 μm. The Rz of the rods 3 is important where the fibre(s) 2 are hair fibre(s) in view of correspondence of the distance between hair fibre cuticles and the average roughness value Rz of the rods 3. The average roughness Rz is average distance between the highest peak (Rp) and lowest valley (Rv) in a sampling length (i.e. Rz=Rp+Rv). Rz is measured in the longitudinal magnification direction of roughness curve and the obtained value is expressed in micrometer (μm). Rz may be calculated according to ASME standard Y14.36M-1996. Surface of rod must be made of a material that will not change e.g. wear, over time. This is because hair is very hard and durable on its outer surface and it can polish material very effectively which is not useful vis-à-vis the present invention since measurements will not be consistent over the lifetime of the device. Therefore, it is advantage if the surface of the rods 3 has been hardened during manufacture.

Example rod 3 that can be used is an ejector pin made according to ISO 6751 (DIN 1530A), steel grade 1.2344, surface roughness Rz 2.5 μm, hardened and tempered 53HRc and supplied by Knarr Werkzeugtechnik.

Fibre-Guiding Means

In at least one embodiment, mounted on each rod 3 is at least one fibre-guiding means 7, or wherein mounted on each rod are two fibre-guiding means 7. The fibre-guiding means 7 is useful for keeping the fibre(s) 2 within the device and for preventing significant lateral movement of the fibre(s) 2 along the length of the rod 3. The fibre-guiding means 7 is useful for negating any disadvantage of the distal end 5 of the rod 3 being free. In at least one embodiment, the fibre-guiding means 7 can freely rotate with its respective rod when the rod is rotated. In at least one embodiment, the fibre-guiding means 7 is firmly attached to its rod 3, or immovably attached to its rod 3 during use. The firm attachment is useful in preventing unnecessary friction fluctuations caused by rotation of the fibre-guiding means 7 around the rod 3. This ensures a negligibly small level of friction of the fibre(s) against the fibre-guiding means 7 with very low friction fluctuation. The instrument disclosed in Vaynberg and Nall has a solid housing on both sides of the rods that is used for hair tress guidance. While pulling the tresses through the instrument disclosed in Vaynberg and Nall, the hair tress is in frictional contact with the housing of the instrument leading to a higher frictional components on the measured value by the housing compared to the present invention. As a consequence the instrument disclosed in Vaynberg and Nall measures more the friction of the hair tress against the housing of the instrument than the present invention and thus the the instrument disclosed in Vaynberg and Nall leads to a higher fluctuation of the measurements compared to the present invention. As a result of this, the measured values using the instrument disclosed in Vaynberg and Nall are not optimally representing the friction on rod and the fibre-fibre interaction in combination with the bending stiffness of the fibre.

In at least one embodiment, the fibre-guiding means 7 is releasably attached to its rod 3. The releasable attachment is useful in that the position of the the fibre-guiding means 7 can thus be adjusted to accommodate a greater or lesser number of fibres 2. In at least one embodiment, mounted on each rod 3 are two fibre-guiding means 7 and wherein the fibre-guiding means 7 are located either side of the fibre(s) 2. In at least one embodiment, the fibre-guiding means 7 is disc-shaped.

Figure 10:
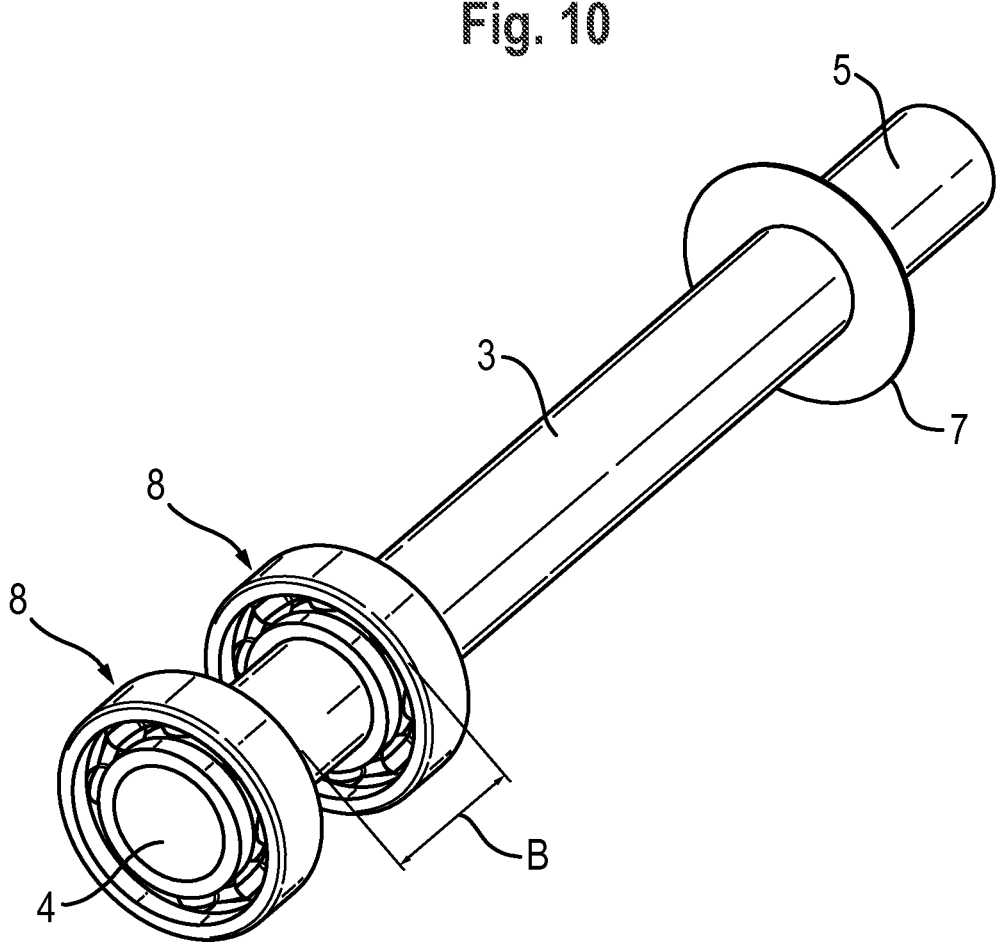
FIG. 10: A rod 3 is depicted. Two housings 8 comprising ball bearings 9 are attached to the rod 3. The distance between the housings 8 is depicted as distance B. Also attached to the rod 3 is a fibre-guiding means 7.
Figure 11:
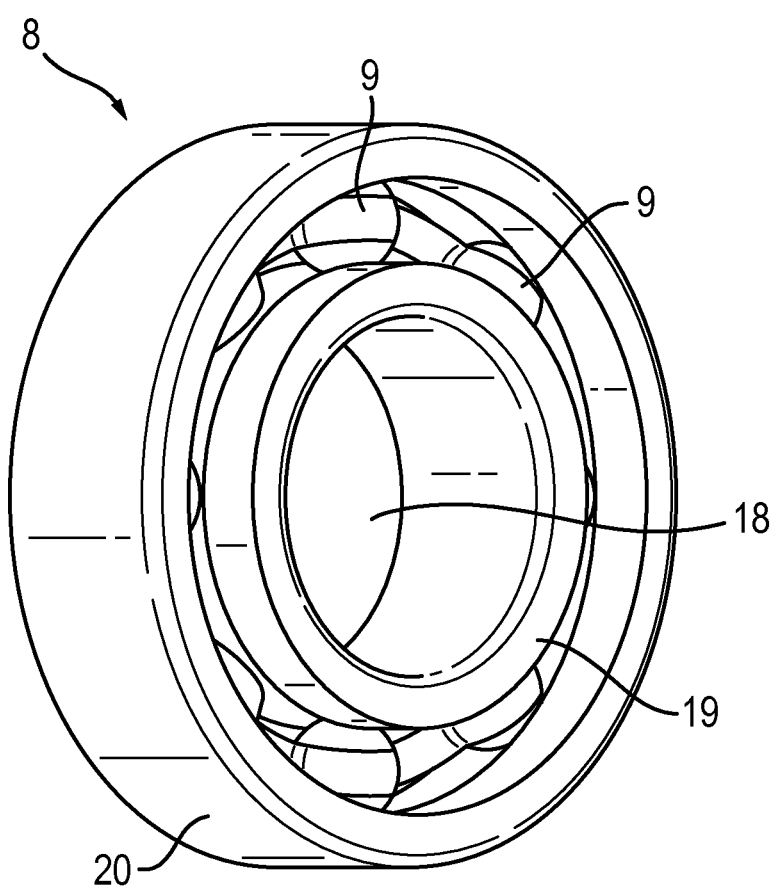
FIG. 11: A housing 8 comprising ball bearings 9.

In at least one embodiment, the fibre-guiding means 7 has a total diameter F. In at least one embodiment, the total diameter F is from 0.5 cm to 10 cm, or from 0.5 cm to 1 cm. The shape and size of the fibre-guiding means is useful in providing the optimal balance between effective fibre guiding. A smaller total diameter F has the advantage that the fibre-guiding means can be lighter in weight. In at least one embodiment, the fibre-guiding means 7 is disc-shaped. A disc shape has the advantage that the radius of a disc is constant and therefore when the fibre-guiding means 7 is rotating with its rod 3, no change in friction between fibres 2 and fibre-guiding means 7 due to variations in radius can occur. A disc-shaped fibre-guiding means is illustrated in FIG. 10.

In at least one embodiment, the device 1 is for measuring the properties of a tress of fibres and wherein the fibre-guiding means 7 are located either side of the tress of fibres such that the fibre-guiding means 7 are from 100% to 150% of the tress width apart.

The fibre-guiding means 7 on the rods 3 of the device 1 allows adjustability e.g. to use multiple sizes of hair tresses and while still ensuring a proper tress guidance during use. In contrast to this, the instrument disclosed in Vaynberg and Nall is limited in the tress size in view of the fixed position of the housing which thus limits the resolution of the system. Another advantage of the fibre-guiding means 7 of the present invention is that it allows to precisely position the fibre(s) 2 centrally in alignment under the fibre-pulling means e.g. load cell of an Instron type measurement system.

In at least one embodiment, the fibre-guiding means 7 is composed of a resistant material. In at least one embodiment, the resistant material is selected from the group consisting of: metal, ceramic, and combinations thereof. In at least one embodiment, the resistant material is selected from the group consisting of: aluminium, ceramic, steel, plastics, and combinations thereof. In at least one embodiment, the fibre-guiding means 7 is composed of aluminium. Aluminium has the advantage that it is strong, yet light. Light in weight is useful for the fibre-guiding means 7 because extra weight puts extra pressure on the support for the rods 3.

Suitable fibre-guiding means 7 can be made by shaping metal pieces using a lathe. In at least one embodiment, the fibre-guiding means 7 has a radial thread for attachment to a rod 3.

In at least one embodiment, the fibre-guiding means 7 is coated with a lubricating means. In at least one embodiment, the lubricating means is a hydrophobic compound. In at least one embodiment the majority of the surface area of fibre-guiding means 7 is coated with a fluorocarbon compound. The "majority of the surface area" means greater than 50% of the total surface area. In at least one embodiment, the fibre-guiding means 7 is evenly and uniformly coated with a lubricating means. In at least one embodiment, the fibre-guiding means 7 is coated with polytetrafluoroethylene. Polytetrafluoroethylene is available under the brand name Teflon by the DuPont Company. In at least one embodiment, the surface of the fibre-guiding means 7 has an average roughness value Rz, being from 0.1 μm to 1 μm, or from 0.1 μm to 0.3 μm, or from 0.2 μm to 0.3 μm. Rz has already been defined above.

Support

The proximal end 4 is connected to a support 6. The support 6 provides a solid base for the rods 3. In at least one embodiment, the support 6 is firmly and releasably attached to a base. The base is useful for providing a solid and immovable foundation. The base may be a table or laboratory bench, for example, that is firmly attached to the floor and/or wall via bolts and/or screws. In at least one embodiment, the support 6 elevates the plurality of rods 3 to provide a void 13 for the fibre(s) 2. In at least one embodiment, the support 6 is composed of metal.

Ball Bearings

In at least one embodiment, the distal end of each rod 5 is connected to the support 6 via via a housing 8 comprising a plurality of ball bearings 9. In at least one embodiment, the ball bearings 9 are composed of ceramic. Herein "ceramic" means an inorganic, crystalline material. In at least one embodiment, the ball bearings 9 comprise silicon nitride, or are composed of silicon nitride. In at least one embodiment, the ball bearings 9 are not hollow. Hollow ball bearings may be compressible and/or less robust versus non-hollow i.e. solid ball bearings 9. In at least one embodiment the ball bearings 9 are coated with a lubricating means.

In at least one embodiment, the lubricating means is in solid form, or is non-sticky. Wet lubricating means, e.g. by means of a flowable compound or flowable composition such as (silicon-based) oil or grease, has the disadvantage that the ball bearings typically stick to each other, or any housing 8, when at a standstill. It is advantageous to use lubricating means in solid form because a lower moment (torque) is required in order to rotate the rods 3 than when a wet lubricating means is used.

In at least one embodiment, the lubricating means is a hydrophobic compound. In at least one embodiment, at least a portion of each ball bearing 9 is coated with a fluorocarbon compound, or wherein the majority of the surface area of each ball bearing 9 is coated with a fluorocarbon compound. In at least one embodiment, the ball bearings 9 are coated with a fluorocarbon compound for improved smoothness. The "majority of the surface area" means greater than 50% of the total surface area. In at least one embodiment, the ball bearings 9 are spherical. In at least one embodiment, the ball bearings 9 are evenly and uniformly coated with a lubricating means. In at least one embodiment, the ball bearings 9 are coated with polytetrafluoroethylene. Polytetrafluoroethylene is available under the brand name Teflon® by the DuPont™ Company. It is advantageous to use a hybrid ball bearing consisting of silicon nitride ball bearings that are polytetrafluoroethylene (Teflon®) coated and enclosed in a stainless steel housing 8 because such ball bearings is providing very low friction values even when in a non lubricated state. Very low friction properties of the bearings are important to ensure a negligible level of bearing friction when operating in mode. This enables high precision assessment of inter-fibre friction in combination with the bending stiffness of the fibre. The instrument disclosed in Vaynberg and Nall uses standard ball bearings with a higher level of friction that cause higher variation in the measurement. Such ball bearings are available from Blassinger, Dieselstr. 16, D-74076 Heilbronn, Germany (www.blaessinger.de).

In at least one embodiment, the surface of the ball bearings 9 have an average roughness value Rz being from 0.1 μm to 1 μm, or from 0.1 μm to 0.3 μm, or from 0.2 μm to 0.3 μm. Rz has already been defined above.

In at least one embodiment, the housing 8 is a circular cassette comprising at least six ball bearings 9, or at least eight ball bearings 9. In at least one embodiment, the housing 8 is a circular cassette having a housing orifice 18. In at least one embodiment, the housing orifice 18 is complementary in diameter to the diameter of the rod 3 to which it is connected. In at least one embodiment, the cassette comprises a rim for preventing lateral movement of the ball bearings 9 inside the cassette. In at least one embodiment, the cassette comprises a cover for protecting the ball bearings 9 from dust and other environmental contamination. Such dust and/or environmental contamination, when allowed to contact the ball bearings 9, can lead to wear of the interior of the housing 8. In at least one embodiment, the housing 8 comprises an inner bearing seat 19 and an outer bearing seat 20. In at least one embodiment, the housing orifice 18 is formed by the inner bearing seat 19. In at least one embodiment, the housing 8 is a circular cassette wherein the circular shape is bounded by the outer bearing seat 20.

In at least one embodiment, the distal end of each rod 5 is connected to the support 6 via via two housings 8, wherein each housing 8 comprises a plurality of ball bearings 9. Having two sets of ball bearings 9 is useful for providing stability to the rod 3. The distance between each set of ball bearings 9 from each other—a greater distance provides improved stability of the rod 3. In at least one embodiment, two sets of ball bearings 9 are separated by an average distance B. Distance B is proportional to the stability of the rod 3. In at least one embodiment, the ratio of distance B to average length L (i.e. B:L in cm) is from 1:1.5 to 1:5, or from 1:2 to 1:4, or from 1:2.4 to 1:3.2.

Blocking Mechanism

In at least one embodiment, the device 1 can operate in rotational mode and stationary mode; wherein during the rotational mode, the rods 3 freely rotate; and wherein, during the stationary mode, the rods 3 are not able to rotate at all.

Measurements using the device 1 may be performed in a rotational mode, where the rods (and their attached fibre-guiding means 7) freely rotate, and also in a stationary mode. In the stationary mode, a blocking mechanism 11 has been activated. In stationary mode, the stationary work of pulling is measured. This is the sum of: the bending force needed to bend fibre(s), fibre-fibre friction and the fiction on the rods and fibre-guiding means. In the rotational mode, the device can be used to measure fibre bending force and fibre-fibre friction. Since the rods 3 and fibre-guiding means 7 freely rotate when the device 1 is in the rotational mode, the difference between force in stationary and rotational modes can be used to calculate the friction force on rods 3.

In at least one embodiment, the device 1 comprises a blocking mechanism 11. In at least one embodiment, the blocking mechanism 11 causes the ball bearings to stop moving. In at least one embodiment, the stationary mode is induced by activating a radial blocking mechanism 11. In at least one embodiment, the blocking mechanism 11 is force-controlled. Herein "force-controlled" means that a maximum amount of force applied can be specified and adjusted. A force-controlled radial blocking mechanism 11 is advantageous because it enables measuring the friction force on rods 3 whilst ensuring protection to ball bearings in the long term and thus leads to sustainably high precision in the friction measurement. In contrast to this the instrument of Vaynberg and Nall uses an axial blocking of the rods. The blocking mechanism in the instrument of Vaynberg and Nall is also not force-controlled, thus high axial force will be applied on any ball bearings used. A too high axial force on ball bearings can lead to dents in the bearing shells this can cause cold welding of steel ball bearing to any housing surround the steel ball bearing or to each other. This is damaging the bearing and resulting in higher friction values of the bearing which decreases the sensitivity of the instrument. In view of the axial blocking mechanism, lower differentiation of the measured hair properties will result for the instrument of Vaynberg and Nall versus the present invention, and this differentiation will worsen over time and/or require frequent ball bearing replacement.

The blocking mechanism 11 can be provided by and/or composed of any material that is hard enough such that the rods 3 are not able to rotate e.g. any ball bearings 9 are not able to move. In at least one embodiment, the blocking mechanism 11 is composed of stainless steel, aluminium, carbon fibres, resistant plastics.

In at least one embodiment, the force controlled radial blocking mechanism 11 is activated with a blocking lever 12. The blocking lever 12 is designed to allow the user to switch between modes quickly and thus handle the device more precisely and easily.

In at least one embodiment, the blocking lever 12 activates plates 14 such that they meet or hug a cap 15. In at least one embodiment, cap 15 is attached to the proximal end 4 of rod 3. In at least one embodiment, all rods 3 have a cap 15 attached to the proximal end 4. In at least one embodiment, the plate 14 comprises a roughened portion 17 where it meets cap 15. The roughened portion 17 may for example be a foam strip. The blocking lever 12 may act like the quick-release means used for attaching modern bicycle wheels to the frame/forks. In at least one embodiment, a pin 16 connects plates 14. In at least one embodiment, cap 15 has a surface roughness Rz of from 0.5 mm to 2 mm, or from 1 mm to 1.5 mm, or 1 mm. Rz has already been defined above.

Fibre-Pulling Means

In at least one embodiment, the fibres 2 are passed through the device 1 using a fibre-pulling means 10. In at least one embodiment, the fibre-pulling means 10 is able to pull at a constant rate and simultaneously measure force. Any commercially available load extension measurement system on the market is suitable, for example a Texture Analyser may be used. Systems from Instron are particularly suitable. For example, Instron model no.: 3343 and Bluehill Software version: 2.32.881.

In at least one embodiment, the fibre-pulling means 10 passes the fibre(s) 2 through the device 1 at a velocity of from 500 to 2000 mm/min.

Fibre(s)

The device 1 is for testing the properties of fibre(s) 2. In at least one embodiment, the device is for testing the properties of a tress of fibres 2. In at least one embodiment, the tress comprises at least five fibres 2. In at least one embodiment, the tress comprises at least 25, or at least 50, or at least 75, or at least 100 fibres 2. In at least one embodiment, the tress is from 2 cm to 10 cm wide. In at least one embodiment, the tress is from 2 cm to 3 cm wide, or from 3 cm to 7 cm wide. In at least one embodiment, the fibres 2 are keratin fibres. In at least one embodiment, the fibres 2 are human scalp hair fibres.

Assembly

Figure 4:
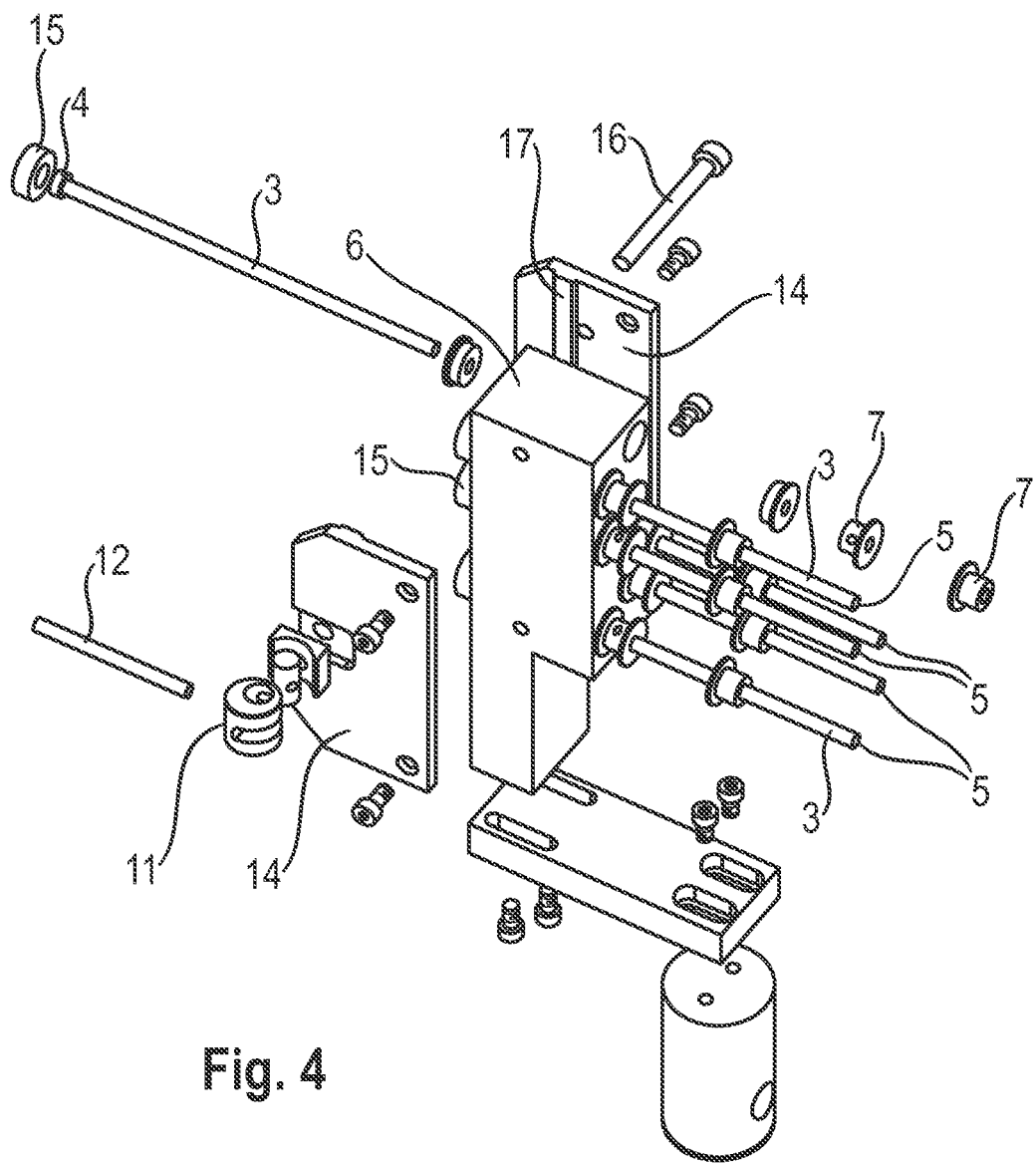
FIG. 4: Device 1 as in FIG. 1, but exploded view.

An exploded view of the assembly of the device 1 is shown in FIG. 4. The housing 8 for the ball bearings 9 is inserted into the support 6 before the rods 3 are inserted into the orifice 18 of the housing 8. When mounting the housing 8 comprising ball bearings 9 into the drilled holes of the support 6 one has to take special care to avoid axial loads on the ball bearings 9. When pushing the rods 3 through the orifice of the housing 8 for the ball bearings 9 one has to take care that this is done in a way that only the inner bearing seat 19 is applied with load. When inserting/mounting the housing 8 for the ball bearings 9 into the support 9 load should be applied to the outer bearing seat 20 only. It is not useful to use any type of glue for fixing the housing 8 for the ball bearings 9 to the support 6.

Measurements and Calculations

Cleaning of device 1, particularly the rods 3, is important for accurate measurements and for reliable measurements over time. Various solvents and solvent mixtures can be used. The exact solvent used depends on material used e.g. for the rod 3, which must not be damaged or eroded by the solvent. Any ball bearings must also be protected from any cleaning means.

The device can be used to measure to two values—the rotational work of pulling ($W^{rotational}$) and the stationary work of pulling ($W^{stationary}$). The rotational work of pulling ($W^{rotational}$) that is measured measures the sum of the work of fibre-fibre friction ($W^{fibre\text{-}fibre\ friction}$) and work of fibre stiffness ($W^{fibre\ stiffness}$). The work of fibre stiffness is the work caused by bending a fibre(s). The work of fibre-fibre friction is the work caused by the rubbing together of a plurality of fibres. The difference in force measured in rotational mode versus stationary mode depends on the friction of the fibre(s) passing over the rods—in other words, fibres with a rough surface would result in a greater difference in the rotational work of pulling ($W^{rotational}$) and the stationary work of pulling ($W^{stationary}$) versus the same fibres but with a much glossier surface. Thus the friction of the fibre(s) passing over the rods ($W^{friction\ on\ rods}$) can be calculated using the below formula:

$$W^{friction\ on\ rods} = W^{stationary} - W^{rotational}$$

Such $W^{friction\ on\ rods}$ is the same as the surface friction of the fibre(s). The surface friction varies with hair type, hair fibre diameter, hair damage level, and also with the type and amount of hair treatment agent used on the hair such as rinse of conditioner, leave-on conditioner, hair styling product e.g. gel, sprays, mousse etc. In other words, such calculation allows the assessment of various criteria, for example hair treatment agent efficacy and hair damage level.

Exemplary Embodiments of the First Aspect

At least one embodiment relates to a device 1 for testing the properties of fibre(s) 2 comprising: a plurality of rods 3 that are capable of freely rotating; wherein each rod 3 has a proximal end 4 and a distal end 5; wherein the proximal end 4 is connected to a support 6; characterised in that the distal end 5 is free; and wherein the device 1 comprises at least five rods 3; and wherein mounted on each rod 3 is at least two fibre-guiding means 7; and wherein the distal end of each rod 5 is connected to the support 6 via a housing 8 comprising a plurality of ball bearings 9; and wherein the ball bearings 9 are composed of silicone nitride, and wherein the wherein the ball bearings 9 are coated with a fluorocarbon compound. In at least one embodiment, the device 1 comprises from two to eight rods 3. In at least one embodiment, the plurality of rods 3, in concert, form two rows when viewed from the distal end 5 side of the rods 3.

At least one embodiment relates to a device 1 for testing the properties of fibre(s) 2 comprising: a plurality of rods 3 that are capable of freely rotating; wherein each rod 3 has a proximal end 4 and a distal end 5; wherein the proximal end 4 is connected to a support 6; characterised in that the distal end 5 is free; and wherein the device 1 comprises at least five rods 3; and wherein mounted on each rod 3 is at least two fibre-guiding means 7; and wherein the fibre-guiding means 7 are disc-shaped; and wherein the distal end of each rod 5 is connected to the support 6 via via two housings 8, wherein each housing 8 comprises a plurality of ball bearings 9.

At least one embodiment relates to a device 1 for testing the properties of fibre(s) 2 comprising: a plurality of rods 3 that are capable of freely rotating; wherein each rod 3 has a proximal end 4 and a distal end 5; wherein the proximal end 4 is connected to a support 6; characterised in that the distal end 5 is free; and wherein the device 1 comprises at least five rods 3; and wherein mounted on each rod 3 is at least two fibre-guiding means 7; and wherein the fibre-guiding means 7 are disc-shaped; and wherein the distal end of each rod 5 is connected to the support 6 via via two housings 8, wherein each housing 8 comprises a plurality of ball bearings 9; and wherein the device 1 can operate in rotational mode and stationary mode; wherein during the rotational mode, the rods 3 freely rotate; and wherein, during the stationary mode, the rods 3 are not able to rotate at all. In at least one embodiment, the plurality of rods 3, in concert, form an S-shape when viewed from the distal end 5 side of the rods 3, or the mirror image of an S shape.

2$^{nd}$ Aspect—Use

The second aspect relates to the use of a device 1 according to the first aspect for testing the properties of fibres 2. The description of the features of the first aspect above is compatible to the present 2$^{nd}$ aspect i.e. can be used in the use of the device 1 for testing the properties of fibres 2. At least one embodiment relates to the use of the device 1 according to the first aspect for testing the mechanical properties, such as stiffness and flexibility, of fibres 2. At least one embodiment relates to the use of the device 1 according to the first aspect for testing the surface roughness of fibres 2. At least one embodiment relates to the use of the device 1 according to the first aspect for testing the conditioning effect of conditioning formulations on fibres 2. At least one embodiment relates to the use of the device 1 according to the first aspect for testing the effect of colour and/or dye treatments on fibres 2. At least one embodiment relates to the use of the device 1 according to the first aspect for testing the effect of styling products, such as perming and straightening treatments, on fibres 2. At least one embodiment relates to the use of the device 1 according to the first aspect for testing the effects of treatments for chemically modifying the fibre(s) 2.

In at least one embodiment of the use, the device 1 operates in rotational mode and stationary mode; wherein during the rotational mode, the rods 3 freely rotate; and wherein, during the stationary mode, the rods 3 are not able to rotate at all. In at least one embodiment of the use, the difference between the force in stationary and rotational modes is used to calculate the friction force on rods 3. In at least one embodiment of the use, the device 1 is a device 1 for testing the properties of fibre(s) 2 comprising: a plurality of rods 3 that are capable of freely rotating; wherein each rod 3 has a proximal end 4 and a distal end 5; wherein the proximal end 4 is connected to a support 6; characterised in that the distal end 5 is free; and wherein the device 1 comprises at least five rods 3; and wherein mounted on each rod 3 is at least two fibre-guiding means 7; and wherein the distal end of each rod 5 is connected to the support 6 via a housing 8 comprising a plurality of ball bearings 9; and wherein the ball bearings 9 are composed of silicone nitride, and wherein the wherein the ball bearings 9 are coated with a fluorocarbon compound. In at least one embodiment, the plurality of rods 3, in concert, form an S-shape when viewed from the distal end 5 side of the rods 3, or the mirror image of an S shape.

3$^{rd}$ Aspect—Method

The third aspect relates to a method for testing the properties of fibre(s) 2 comprising: (a) providing a device 1 according to the first aspect, and providing fibres 2; (b) threading the fibres 2 through the plurality of rods 3 between the fibre-guiding means 7; (c) by use of a fibre-pulling means 10, passing the fibres 2 through the device 1 and simultaneously measuring the force required to do this. The description of the features of the first aspect above is compatible to the present 3$^{rd}$ aspect i.e. can be used in the method of using the device. The steps (a) to (c) are carried out in the order (a), then (b) and then (c). In at least one embodiment, the fibre-pulling means 10 passes the fibre(s) 2 through the device 1 at a velocity of from 500 to 2000 mm/min.

In at least one embodiment, the device 1 operates in rotational mode and stationary mode; wherein during the rotational mode, the rods 3 freely rotate; and wherein, during the stationary mode, the rods 3 are not able to rotate at all. In at least one embodiment, the difference between the force in stationary and rotational modes is used to calculate the friction force on rods 3.

In at least one embodiment, the fibre(s) 2 are human hair(s) that have been plucked from a human scalp. In at least one embodiment, the method comprises step (d) providing feedback to the human from which the fibre(s) 2 came from on the health and/or mechanical properties of their hair.

In at least one embodiment of the method, the device 1 of step (a) is a device 1 for testing the properties of fibre(s) 2 comprising: a plurality of rods 3 that are capable of freely rotating; wherein each rod 3 has a proximal end 4 and a distal end 5; wherein the proximal end 4 is connected to a support 6; characterised in that the distal end 5 is free; and wherein the device 1 comprises at least five rods 3; and wherein mounted on each rod 3 is at least two fibre-guiding means 7; and wherein the distal end of each rod 5 is connected to the support 6 via a housing 8 comprising a plurality of ball bearings 9; and wherein the ball bearings 9 are composed of silicon nitride, and wherein the wherein the ball bearings 9 are coated with a fluorocarbon compound. In at least one embodiment, the plurality of rods 3, in concert, form an S-shape when viewed from the distal end 5 side of the rods 3, or the mirror image of an S shape.

Experimental

The effect of a styling treatment on human hair fibre stiffness in the context of a tress of fibres is tested. 5 cm width human hair tresses of 6 g weight are used. All hair tresses used are double bleached prior to use in order to improve normalisation i.e. consistency of hair quality. The pre-treatment is as follows:

Bleaching powder (2.5 g/l g hair) and 9% Welloxon (7.5 ml/l g hair) for 30 min and rinsed with tap water (6 L, 35° C.) for 2 min; subsequently washed twice, each time with 0.25 ml shampoo per 1 g hair for 1 min and rinsed for 2 min; afterwards the tresses are stored in distilled water for 24 h and rinsed once more under tap water (6 L/min, 35° C.) for 2 min; finally the tresses are dried at 20° C. and 65% RH for 48 h.

Three experiment samples are carried out: untreated; placebo treatment; and styling treatment. For each experiment sample, 4 hair tresses are used. In other words, where n=3, this represents the testing of 12 hair tresses for each experiment sample and thus 36 tresses in total. For the untreated experiment sample, no treatment was carried out to the tresses except for the aforementioned pre-treatment. For the placebo treatment and styling treatment, firstly an initiator formulation was applied to the hair:

| Initiator Formulation | |
|---|---|
| Phase 1 | |
| Purified water | 48.00 |
| Disodium phosphate | 0.08 |
| Salicylic acid | 0.10 |
| Phase 2 | |
| Hydrogen peroxide | 2.00 |
| Phosphoric acid | 0.06 |
| Purified water | QSP |
| Total | 100.00 |

On each hair tress, 1 g initiator formulation per 1 g hair is applied and massaged in for 10 sec. The initiator formulation is left on hair for 5 min. Afterwards the remaining initiator formulation on the tress was pressed out with a napkin. The pressing out is normalised by final weight of the tress. For the placebo treatment and styling treatment, as a second step, a placebo formulation and styling formulation, respectively, was applied to the hair:

| | Placebo formulation | Styling formulation |
|---|---|---|
| 3-sulfopropyl acrylate | — | 12.00 |
| Cellosize HEC QP 4400 [1] | 0.20 | 0.20 |
| EDTA | 0.12 | 0.12 |
| Keltrol CG-T [2] | 1.00 | 1.00 |
| Phenoxethol [3] | 1.00 | 1.00 |
| PHB-Methylester [4] | 0.20 | 0.20 |
| Genapol ® C 100 [5] | 0.70 | 0.70 |
| Cremophor EL [6] | 0.70 | 0.70 |
| Fragrance | 0.30 | 0.30 |
| Distilled water | QSP | QSP |
| Total | 100 | 100 |

KEY:
[1] = Hydroxyethylcellulose;
[2] = Xanthan gum (high molecular weight heteropolysaccharide gum produced by a pure-culture fermentation of a carbohydrate with *Xanthomonas campestris*);
[3] = 2-(phenoxy)ethanol;
[4] = methyl paraben;
[5] = Coceth-10 (Coconut oil alcohol, ethoxylated);
[6] = PEG-35 Castor Oil.

1.2 g formulation per 1 g hair is applied on each hair tress and massaged in for 10 sec. After a 30 min at room temperature, the formulation is wiped off with the fingers. Each tress is rinsed with tap water for 1 min (6 L/min, 35° C.) and adjusted to a residual humidity of 50% by weight. Then 0.25 ml Pantene Clarifying Shampoo per 1 g hair is applied and massaged in for 1 min. Afterwards the tress is rinsed with tap water for 1 min (6 L water/min, 35° C.). All treated tresses are combed 10 times with a metal comb (5 times with the coarse side and 5 times with the fine side). The tresses have a residual humidity of 50% per weight. The tresses are placed in stretched condition in a lab dish. The tip ends are weighed down with a plastic spattle to prevent the bending of hair swatch. Finally the swatches are dried in the climatic chamber overnight (20° C., 65% RH).

Each hair tress is passed in a S-shape between the rods of a device according to the present invention (as illustrated in FIGS. 1-3, and 6-8) comprising six rods by means of an Instron at an extension of 400 mm/min. The measurement is executed 5 times in stationary mode and 5 times in rotational mode. The forces exerted are calculated as total work (energy). The work in the rotational mode relates to the hair stiffness.

Significance Tests Using T-Test: Measurement of Stiffness

| Mean energy (mJ) | Standard Deviation | n | Experiment sample | Untreated | Placebo treatment |
|---|---|---|---|---|---|
| 11.03 | 0.052 | 3 | Untreated | | |
| 11.57 | 0.523 | 3 | Placebo treatment | 84.5% | |
| 12.95 | 0.495 | 3 | Styling treament | 99.7% | 97.1% |

>=95% = significant

Conclusions: the presence of 3-sulfopropyl acrylate in the styling formulation versus the placebo formulation causes an increase in stiffness of the hair fibres. 3-sulfopropyl acrylate is a monomer that polymerises to form a polymer inside the hair shaft. This concept has been discussed in WO2009/088520A, WO2012/100006A, WO2012/100007A and EP2295029A. From the present data it is demonstrated that the polymer causes a change in the mechanical properties of the hair fibre—here, hair fibre stiffness increase is demonstrated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A device for testing the properties of fibre(s) comprising:
   a plurality of rods;
   wherein each rod has a proximal end and a distal end;
   wherein the proximal end is connected to a support;
   wherein the distal end is free;
   wherein there is only one support; and
   wherein mounted on each rod is at least one fibre-guiding means wherein the fibre-guiding means is adjustable
   wherein the proximal end of each rod is connected to the support via a housing comprising a plurality of ball bearings;
   wherein the ball bearings are composed of silicon nitride; and
   wherein at least a portion of each ball bearing is coated with a fluorocarbon compound.

2. The device of claim 1, wherein the device comprises at least four rods.

3. The device of claim 1, wherein the fibre-guiding means are located either side of the fibre(s).

4. The device of claim 1, wherein the device is for measuring the properties of a tress of fibres and wherein the fibre-guiding means are located either side of the tress of fibres such that the fibre-guiding means are from about 100% to about 150% of the tress width apart.

5. The device of claim 1, wherein the majority of the surface area of each ball bearing is coated with a fluorocarbon compound.

6. The device of claim 5, wherein the ball bearings are coated with polytetrafluoroethylene.

7. The device of claim 1, wherein the fibre-guiding means is coated with a lubricating means.

8. The device of claim 1, wherein the surface of the fibre-guiding means has an average roughness value Rz being from about 0.1 μm to about 1 μm.

9. The device of claim 8, wherein the surface of the fibre-guiding means has an average roughness value Rz being from about 0.1 μm to about 0.3 μm.

10. The device of claim 8, wherein the surface of the fibre-guiding means has an average roughness value Rz being from about 0.2 μm to about 0.3 μm.

11. The device of claim 1, wherein the plurality of rods, in concert, form an S-shape when viewed from the distal end side of the rods, or the mirror image of an S shape.

12. The device of claim 1, wherein the support is composed of metal.

13. The device of claim 1, wherein the fibre-guiding means is disc-shaped.

14. A method for testing the properties of fibre(s) comprising:
   (a) providing a device of claim 1, and providing fibres;
   (b) threading the fibres through the plurality of rods between the fibre-guiding means;
   (c) by use of a fibre-pulling means, passing the fibres through the device and simultaneously measuring the force required to do this.

* * * * *